United States Patent [19]

Eberlein et al.

[11] Patent Number: 5,011,836
[45] Date of Patent: Apr. 30, 1991

[54] AGENTS FOR THE TREATMENT OF ACUTE AND CHRONIC OBSTRUCTIVE RESPIRATORY PASSAGE DISEASES

[75] Inventors: Wolfgang Eberlein; Wolfhard Engel; Gerhard Mihm; Klaus Rudolf, all of Biberach; Henri Doods, Wathausen; Norbert Mayer, Biberach, all of Fed. Rep. of Germany

[73] Assignee: Dr. Karl Thomae GmbH, Biberach an der Riss, Fed. Rep. of Germany

[21] Appl. No.: 438,827

[22] Filed: Nov. 17, 1989

[30] Foreign Application Priority Data

Nov. 17, 1988 [DE] Fed. Rep. of Germany ....... 3838912

[51] Int. Cl.$^5$ ............................................ A61K 31/55
[52] U.S. Cl. ..................................... 514/217; 514/826
[58] Field of Search ......................................... 514/217

[56] References Cited

U.S. PATENT DOCUMENTS 4,567,178 1/1986 Eberlein et al. .................... 514/215

Primary Examiner—Leonard Schenkman
Attorney, Agent, or Firm—David E. Frankhouser; Daniel Reitenbach; Mary-Ellen M. Timbers

[57] ABSTRACT

A method for treating abstructive respiratory passage disorders which comprises the use of 5,11-dihydro-11-[[(1-methyl-4-piperidinyl)-amino]carbonyl]-6H-dibenz[b,e]azepin-6-one; 5,11-dihydro-11-[(1-methyl-4-piperazinyl)acetyl]-6H-dibenz[b,e]azepin-6-one, 5,11-dihydro-11-[(4-methyl-1-piperazinyl)acetyl]-6H-dibenz[b,e]azepin-6-one, alone or in combination.

4 Claims, No Drawings

AGENTS FOR THE TREATMENT OF ACUTE AND CHRONIC OBSTRUCTIVE RESPIRATORY PASSAGE DISEASES

The invention relates to agents for the treatment of acute and chronic obstructive respiratory passage diseases, which agents contain the compounds
5,11-dihydro-11-[[(1-methyl-4-piperidinyl)amino]carbonyl]-6H-dibenz[b,e]azepine-6-one and/or
5,11-dihydro-11-[(1-methyl-4-piperidinyl)acetyl]-6H-dibenz[b,e]azepin-6-one and/or
5,11-dihydro-11-[(4-methyl-1-piperazinyl)acetyl]-6H-dibenz[b,e]azepin-6-one,
their active enantiomers and/or their physiologically acceptable salts with inorganic or organic acids.

In DE-A-3402060.8 (corresponds to U.S. Pat. No. 4567178), compounds have been described which, as $M_1$- selective muscarinic receptor antagonists have gastric acid secretion-inhibiting properties and thus can be employed advantageously for the treatment of gastric and intestinal disorders.

It has now surprisingly been found that the compounds contained in the above-mentioned patents
A = 5,11-dihydro-11-[[(1-methyl-4-piperidinyl)amino]-carbonyl]-6H-dibenz[b,e]azepin-6-one,
B = 5,11-dihydro-11-[(1-methyl-4-piperidinyl)acetyl]-6H-dibenz[b,e]azepin-6-one,
C = 5,11-dihydro-11-[(4-methyl-1-piperazinyl)acetyl]-6H-dibenz[b,e]azepin-6-one,
and their physiologically active enantiomers, for example the compound
D = (+)-5,11-dihydro-11-[[(1-methyl-4-piperidinyl)amino]carbonyl]-6H-dibenz[b,e]azepin-6-one,
and their physiologically acceptable salts with inorganic or organic acids have further totally different pharmacological properties which make possible their use for the treatment of acute and chronic obstructive diseases of the respiratory passages.

In the literature, it is described in detail that asthma attacks, and thus also chronic bronchitis and emphysema, can be treated using non-selective antimuscarinics, such as atropine.

A great disadvantage of the systemic use of non-selective antimuscarinics is the high rate of non-tolerable anticholinergic side effects such as mydriasis, inhibition of salivation, constipation and serious CNS effects. These side effects exclude the use of non-selective antimuscarinics in systemic therapy.

Surprisingly, in contrast to atropine, a marked selectivity for the inhibition of the bronchoconstriction induced by exogenously administered acetylcholine was found for the above-mentioned substances A, B and C and their enantiomers, in particular their (+)-enantiomers. The large gap between desired effects on the bronchi and the undesired anticholinergic effects (heart, bladder) makes possible the systemic use of the compounds A, B and C and their enantiomers and also their physiologically acceptable salts in various forms of obstructive respiratory passage disorders, without non-tolerable side effects having to be taken into account.

The broncholytic effects described here can be traced back to a selective blockade of muscarinic receptors which are localised on the smooth musculature of the respiratory passages. These muscarinic receptors are also designated as $M_{SM}$ receptors.

Moreover, the above-mentioned substances A, B and C and their enantiomers, in particular the substance D, show a marked $M_1$-selectivity in receptor binding studies. $M_1$-receptors are localised in the parasympathetic ganglia, the post-ganglionic neurones of which supply the smooth musculature of the respiratory passages. A blockade of these $M_1$-receptors leads to an inhibition of the transmission of stimulation from pre- to post-ganglionic neurones, which leads to a decrease of the vagally conditioned bronchial tone or to an inhibition of reflex bronchoconstriction.

The effects of the above-mentioned compounds mediated by $M_1$-receptor blockade thus additionally make a substantial contribution to the activity in the treatment of obstructive disorders of the respiratory passages.

This combination of blockade of the $M_{SM}$ receptors of the respiratory passages and the blockade of the ganglionic $M_1$-receptors leads to a higher activity and thus opens up new therapeutic perspectives in the treatment of chronic and acute disorders of the respiratory passages.

The following tests show the favourable properties of the compounds A, B, C and D.

A. Binding studies on muscarinic receptors

Determination of the $IC_{50}$ value in vitro

Sprague-Dawley rats having body weights of 180-220 g were used as organ donors. After removing the heart, submandible and cerebral cortex, all further steps were carried out in ice-cold Hepes-HCl buffer (pH 7.4; 100 m molar NaCl, 10 m molar $MgCl_2$). The entire heart was comminuted using a pair of scissors. All organs were then homogenised in a Potter.

For the binding test, the organ homogenates were diluted in the following manner(ratio by volume):

| | |
|---|---|
| Entire heart | 1:400 |
| Cerebral cortex | 1:500 |
| Submandible | 1:400 |

The incubation of the organ homogenates was carried out at a defined concentration of the radioligand and a number of concentrations of the non-radioactive test substances in Eppendorf centrifuge tubes at 30° C. The incubation period was 45 minutes. 0.3 nanomolar $^3$H-N-methylscopolamine ($^3$H-NMS, heart and submandible) or 1 nanomolar $^3$H-pirenzepine ($^3$H-PZ, cerebrum) were used as the radioligand. The incubation was ended by addition of ice-cold buffer with subsequent vacuum filtration. The filter was washed with cold buffer and its radioactivity was determined. This represents the total of specific and non-specific binding of $^3$H-NMS or $^3$H-PZ. The proportion of non-specific binding was defined as that radioactivity which was bound in the presence of $1\mu$ molar quinuclidinylbenzylate. Four-fold determinations were always carried out. The $IC_{50}$ values of non-labelled test substances were determined graphically. They represent that concentration of the test substance at which the specific binding of $^3$H-NMS or $^3$H-PZ to the muscarinic receptors in the various organs was inhibited by 50%. The results can be seen from Table I.

B. Inhibition of the effect of acetylcholine on bronchi, bladder and heart rate 5 minutes after administration of the test substance to anaesthetised guinea-pigs, 10 $\mu$g/kg of acetylcholine was injected intravenously and, at the same time, intra-arterially. At the same time, the heart rate was recorded by extracorporeal derivation of the ECG, the respiratory passage resistance by Konzett-Rössler and the contraction of the exposed bladder directly. For the inhibition of the effect of acetylcholine on the organs examined, dosage-activity curves were recorded and $-\log ED_{50}$ values were determined therefrom. For results see Table II.

TABLE I

| | Receptor Binding Tests, in vitro: | | |
| --- | --- | --- | --- |
| | $IC_{50}$ [n Mol $l^{-1}$] | | |
| Substance | $^3$H-PZ Cortex ($M_1$) | $^3$H-NMS Heart ($M_2$) | $^3$H-NMS Submandible ($M_3$) |
| Atropine | 1.0 | 3.0 | 2.0 |
| A | 6.0 | 400 | 70 |
| B | 2.5 | 42 | 13 |
| C | 8.0 | 800 | 100 |
| D | 3.0 | 300 | 50 |

The results of Table I show that the compounds A, B, C and D differ between muscarinic receptors of various tissues.

Unlike atropine, the compounds A, B, C and D show lower $IC_{50}$ values for the cortex $M_1$ receptor compared to muscarinic receptors in preparations of the heart and submandible.

TABLE II

| Inhibition of the effect of acetylcholine on the bladder, bronchi and heart rate of the guinea-pig: | | | |
| --- | --- | --- | --- |
| | $-\log DE_{50}$ (mol/kg) | | |
| Substance | Bronchi | Heart | Bladder |
| Atropine | 7.96 | 7.70 | 7.89 |
| A | 7.26 | 6.02 | 6.27 |
| B | 6.74 | 6.07 | 6.09 |
| C | 6.56 | 5.75 | 5.27 |
| D | 7.48 | 6.39 | 6.51 |

From the pharmacological data of the above Table II, it follows that the bronchoconstriction is inhibited by the compounds A, B, C and D even at dosages at which no effects on the heart and bladder are observed. In contrast to this, atropine shows no selectivity.

In summary, it can be said that the test results for the compounds A, B, C and D prove that they show an $M_1$-selectivity in in vitro receptor binding studies and that the substances more strongly inhibit the cholinergically induced bronchoconstriction in functional tests than frequency effects on the heart or the bladder contraction. This $M_1$ and $M_{SM}$-bronchoselectivity makes possible the systemic treatment of diseases which are characterised by an airway obstruction, for example for the treatment of all forms of asthma, chronic bronchitis and emphysema.

The compounds A, B, C, D, their physiologically active enantiomers and their physiologically acceptable salts with inorganic or organic acids can be used for the above-mentioned purposes both as monopreparations and in combination with one another. For this purpose, the compounds A, B, C, D and their enantiomers are incorporated in a manner known per se into the customary pharmaceutical preparation forms, for example into solutions, solutions for injection, solutions for inhalation, suppositories, tablets, coated tablets or capsules.

Dosages

The daily dose on intravenous administration is in general between 0.010 to 0.15 mg/kg, preferably 0.02 and 0.1 mg/kg, and on oral administration between 0.10 to 1.5 mg/kg, preferably 0.2 and 1.0 mg/kg, of body weight, which is optionally administered in the form of a number, preferably 1 to 3, of individual doses to achieve the desired result.

The compounds A, B and C are prepared as described in U.S. Pat. No. 4,567,178.

The compounds A, B and C in this case exist as racemates.

It has now been found that, for example, in the case of the substance A, the enantiomer having the specific optical rotation of $[\alpha]_D^{20} = +290.8$ (c=0.5; in methanol) represents the biologically active form.

The separation of the racemate into the optically active antipodes can be carried out by known methods, for example using an optically active acid. Suitable optically active acids, in particular are L-(+)- or D-(−)-tartaric acid, one of its derivatives, such as (+)- or (−)-diacetyltartaric acid, (+)- or (−)-monomethyltartrate as well as (+)-camphoric acid.

In the synthesis of the (+)-enantiomer of the compound A, separation has even proved favourable at the stage of the starting compound 5,11-dihydro-11-[6H-dibenz-[b,e]azepin-6-one]-carboxylic acid. This (+)-11-dihydro-11-[6H-dibenz[b,e]azepin-6-one]-carboxylic acid, after reaction with 4-amino-1-methyl-piperidine, gives the desired (+)-enantiomer D of the compound A using methods which proceed without racemisation.

The separation of the racemic 5,11-dihydro-11-[6H-dibenz[b,e]azepin-6-one]-carboxylic acid into its two enantiomers is carried out using an optically active base; those which are suitable are in particular quinine, quinidine or R-(+)- and S-(−)-N,N-dimethyl-phenyl-ethylamine and R-(+)- and S-(−)-α-methylbenzylamine.

The racemic 5,11-dihydro-11-[6H-dibenz[b,e]azepin6-one]-carboxylic acid is reacted in equimolar amounts in a solvent with one of the above-mentioned optically active bases; the crystalline, diastereomeric salts thus obtained are then separated utilising their different solubilities in certain solvents. This separation can be carried out in any suitable solvent, as long as this shows a satisfactory difference in the solubility of the salts. Methanol, ethanol or their mixtures, for example in a volume ratio of 4:1, are preferably used.

The enantiomeric compound D can be prepared by methods (a) and (b) from the salts thus obtained without a racemisation occurring during the reaction:

(a) by liberation of the (+)-5,11-dihydro-11-[6H-dibenz[b,e]azepin-6-one]-carboxylic acid and reaction of this in the presence of N-methylmorpholine and isobutyl chloroformate with 1-methyl-4-amino-piperidine at temperatures from 0° C. to −60° C. or (b) by direct reaction of the salts, for example the quinine salts, in the presence of 4-methylmorpholine and isobutyl chloroformate, with 1-methyl-4-amino-piperidine, optionally in an organic solvent, at temperatures between 0° C. and −60° C.

Of course, the racemates of the compounds A, B and C can also be separated into their (+) and (−) forms according to the methods described in U.S. Pat. No. 4,567,178.

The following Examples are intended to illustrate the preparation of the above-mentioned carboxylic acid and the above-mentioned procedures (a) and (b) for its further processing:

EXAMPLE 1

(+)-5,11-Dihydro-11-[6H-dibenz[b,e]azepin-6-one]-carboxylic acid 101.3 g (0.4 mol) of (±)-5,11-dihydro-11-[6H-dibenz[b,e]azepin-6-one]-carboxylic acid are suspended in 1000 ml of a methanol/ethanol mixture (volume ratio: 4:1) and the mixture is added dropwise at 60° C. to a hot solution of 129.6 g (0.4 mol) of quinine in 900 ml of methanol/ethanol (volume ratio: 4:1). A diastereomeric quinine salt, which contains the (+)-form in a 70:30 enrichment, crystallises out of this solution on cooling. After suction filtering, the quinine salt is recrystallised analogously six more times with the same solvent mixture of methanol/ethanol=4:1 (v:v). After a total of seven crystallisations, 24 g of a quinine salt of melting point 195° C. (dec.), which contains the (+)-5,11-dihydro-11-[6H-dibenz[b,e]azepin-6-one]-carboxylic acid in optically pure form, are obtained.

In order to obtain the free (+)-carboxylic acid, 1.0 g (1.7 mmol) of the quinine salt are suspended in 30 ml of water and the mixture is acidified using dilute hydrochloric acid. The precipitate obtained is suction filtered, washed with water and dried at 30° C.

The optically pure (+)-carboxylic acid melts at 250°-251° C.

EXAMPLE 2

Direct reaction of the quinine salt of (+)-5,11-dihydro-11-[6H-dibenz[b,e]azepin-6-one]-carboxylic acid for the preparation of (+)-5,11-dihydro-11-[[(1-methyl-4-piperidinyl)amino]-carbonyl]-6H-dibenz[b,e]azepin-6-one 11.4 g (0.02 mol) of the quinine salt of (+)-5,11-dihydro-11-[6H-dibenz[b,e]azepin-6-one]-carboxylic acid are suspended in 1000 ml of tetrahydrofuran and 2.0 g (0.02 mol) of 4-methyl-morpholine are added. After cooling to −40° C., 5.4 g (0.04 mol) of isobutyl chloroformate are added. The mixture is stirred at the same temperature for 30 minutes. A solution of 5.04 g (0.044 mol) of 4-amino-1-methyl-piperidine in 20 ml of absolute tetrahydrofuran is then allowed to drip into the reaction mixture. The mixture is stirred for a further hour with cooling and allowed to stand for a further 2 hours. The reaction mixture is concentrated on a rotary evaporator at 40° C. The residue obtained is dissolved in methylene chloride, washed with water and dried over magnesium sulphate. After concentrating, a foamy product is obtained which is made to crystallise by digesting in ethyl acetate.

A colourless product of melting point 250°-251° C. having an optical rotation of $[\alpha]_D^{20} = +290.8$ (c=0.5, methanol) is obtained.

Yield: 2.0 g (28.6% of theory).

EXAMPLE 3

Reaction of (+)-5,11-dihydro-11-[6H-dibenz[b,e]azepin-6-one]-carboxylic acid for the preparation of (+)-5,11dihydro-11-[[(1-methyl-4-piperidinyl)amino]carbonyl]-6H-dibenz[b,e]azepin-6-one 3.9 g (0.015 mol) of (+)-5,11-dihydro-11-[6H-dibenz[b,e]azepin-6-one]-carboxylic acid are suspended in 300 ml of tetrahydrofuran and 1.5 g (0.015 mol) of N-methylmorpholine are added. The mixture is cooled to −40° C. and 2.04 g (0.015 mol) of isobutyl chloroformate, dissolved in 40 ml of tetrahydrofuran, are allowed to drip into this reaction mixture. The mixture is stirred for 30 minutes at the same temperature and then a solution of 1.89 g (0.016 mol) of 4-amino-1-methylpiperidine in 30 ml of tetrahydrofuran is slowly added. The mixture is stirred for another hour with cooling and then allowed to come to ambient temperature. The batch is concentrated on a rotary evaporator at 40° C. After recrystallising from ethyl acetate, the product obtained is completely identical to the product obtained according to Example 2.

Yield: 2.3 g (38.2% of theory).

The optical purity of the final product obtained was checked by HPLC on chiral support material.

It was possible to detect that the content of (+)-form is above 99% and the (−)-enantiomer occurs as less than 1%.

The following Examples illustrate the preparation of pharmaceutical administration forms:

EXAMPLE I

Tablets containing 25 mg of (+)-5,11-dihydro-11-[[(1-methyl-4-piperidinyl)amino]carbonyl]-6H-dibenz[b,e]azepin-6-one

| Composition: 1 Tablet contains | |
|---|---|
| Active substance | 25.0 mg |
| Lactose | 148.0 mg |
| Potato starch | 65.0 mg |
| Magnesium stearate | 2.0 mg |
| | 240.0 mg |

Preparation process:

A 10% strength slurry is prepared from potato starch by warming. The active substance, lactose and the remaining potato starch are mixed and granulated through a sieve of mesh width 1.5 mm with the above slurry. The granules are dried at 45° C., rubbed through the above sieve again, mixed with magnesium stearate and pressed to give tablets.

| Tablet weight: | 240 mg |
|---|---|
| Punch: | 9 mm |

EXAMPLE II

Coated tablets containing 25 mg of (+)-5,11-dihydro-11-[[(1-methyl-4-piperidinyl)amino]carbonyl]-6H-dibenz[b,e]azepin-6-one The tablets prepared according to Example I are coated by known processes with a coating which consists essentially of sugar and talc. The prepared coated tablets are polished with the aid of beeswax. Coated tablet weight: 300 mg

EXAMPLE III

Ampoules containing 1 mg of (+)-5,11-dihydro-11-[[(1-methyl-4-piperidinyl)amino]carbonyl]-6H-dibenz[b,e]azepin-6-one hydrochloride

| Composition: 1 ampoule contains: | |
|---|---|
| Active substance | 1.0 mg |
| Sodium chloride | 8.0 mg |
| Distilled water ad | 1 ml |

Preparation process:

The active substance and sodium chloride are dissolved in distilled water and then made up to the given volume. The solution is sterile filtered and filled into 1 ml ampoules. Sterilisation: 20 minutes at 120° C.

EXAMPLE IV

Suppositories containing 25 mg of 5,11-dihydro-11-[(4-methyl-1-piperazinyl)acetyl]-6H-dibenz[b,e]azepin-6-one

| Composition: 1 suppository contains: | |
|---|---|
| Active substance | 5.0 mg |
| Suppository material (e.g. Witepsol W 45 ®) | 1 695.0 mg |
| | 1 700.0 mg |

Preparation process:

The finely pulverised active substance is suspended in suppository material which has been melted and cooled to 40° C. The material at 37° C. is poured into slightly pre-cooled suppository moulds. Suppository weight: 1.7 g

EXAMPLE V

Drops containing 0.5 g of 5,11-dihydro-11-[[(1-methyl-4-piperidinyl)amino]carbonyl]-6H-dibenz[b,e]azepin-6-one hydrochloride

| Composition: 100 ml of drop solution contain: | |
|---|---|
| methyl p-hydroxybenzoate | 0.035 g |
| propyl p-hydroxybenzoate | 0.015 g |
| Aniseed oil | 0.05 g |
| Menthol | 0.06 g |
| Ethanol, pure | 10.0 g |
| Active substance | 0.5 g |
| Sodium cyclamate | 1.0 g |
| Glycerol | 15.0 g |
| Distilled water ad | 100.0 ml |

Preparation process

The active substance and sodium cyclamate are dissolved in about 70 ml of water and glycerol is added. The p-hydroxybenzoic acid esters, aniseed oil and menthol are dissolved in ethanol and this solution is added with stirring to the aqueous solution. The mixture is finally made up to 100 ml with water and filtered free from suspended particles.

EXAMPLE VI

Metered aerosol metering 100 μg of 5,11-dihydro-11-[[(1-methyl-4-piperidinyl)amino]carbonyl[-6H-dibenz[b,e]azepin-6-one hydrochloride

| One container (150 puffs) contains: | |
|---|---|
| Active substance | 15.0 mg |
| Ethanol | 990.0 mg |
| Propellant gas 12/14 (60:40, v:v) | 8,895.0 mg |
| | 9,900.0 mg |

Preparation process:

The active substance is dissolved in ethanol, and the solution is cooled to 31 30° C. and filled into a precooled aluminium container. The propellant gas mixture cooled to −50° C. is then metered in, and the valve is put on and immediately sealed.

One puff contains 0.1 mg of 5,11-dihydro-11-[[(1-methyl-4-piperidinyl)amino]carbonyl]-6H-dibenz[b,e]azepin-6-one hydrochloride.

What is claimed is:

1. A method for the treatment of obstructive respiratory passage disorders in a patient which comprises administering to the patient a therapeutically effective amount of an agent selected from the group consisting of 5,11-dihydro-11-[[(1-methyl-4-piperidinyl)-amino]-carbonyl]-6H-dibenz[b,e]azepin-6-one (Compound A); 5,11-dihydro-11-[(1-methyl-4-piperidinyl)acetyl]-6H-dibenz[b,e]azepin-6-one (Compound B); 5,11-dihydro-11-[(4-methyl-1-piperazinyl)acetyl]6H-dibenz[b,e]azepin-6-one (Compound C); a combination of Compound A and Compound B; a combination of Compound A and Compound C; a combination of Compound B and Compound C; and a combination of Compound A, Compound B and Compound C, or a physiologically active enantiomer of the agent, or a physiologically acceptable salt of the agent with an inorganic or organic acid.

2. A method as recited in claim 1 wherein the obstructive respiratory passage disorder is asthma, chronic bronchitis or emphysema.

3. A method as recited in claim 1 wherein the agent is (+)-5,11-dihydro-11-[[(1-methyl-4-piperidinyl)amino]-carbonyl]-6H-dibenz[b,e]azepin-6-one or a physiologically acceptable salt thereof with an inorganic or organic acid.

4. A method as recited in claim 3 wherein the obstructive respiratory passage disorder is asthma, chronic bronchitis or emphysema.

* * * * *